United States Patent
Moszner et al.

(10) Patent No.: US 10,195,121 B2
(45) Date of Patent: Feb. 5, 2019

(54) PHOTOPOLYMERIZABLE AND DUAL-CURING DENTAL MATERIALS BASED ON THIOUREA DERIVATIVES

(71) Applicant: Ivoclar Vivadent AG, Schaan (LI)

(72) Inventors: Norbert Moszner, Mauren (LI); Peter Burtscher, Rankweil (AT); Alexandros Gianasmidis, Balgach (CH)

(73) Assignee: Ivoclar Vivadent AG, Schaan (LI)

( * ) Notice: Subject to any disclaimer, the term of this patent is extended or adjusted under 35 U.S.C. 154(b) by 93 days.

(21) Appl. No.: 15/127,428

(22) PCT Filed: Mar. 19, 2015

(86) PCT No.: PCT/EP2015/055858
§ 371 (c)(1),
(2) Date: Sep. 20, 2016

(87) PCT Pub. No.: WO2015/140276
PCT Pub. Date: Sep. 24, 2015

(65) Prior Publication Data
US 2017/0128328 A1  May 11, 2017

(30) Foreign Application Priority Data
Mar. 20, 2014 (EP) .................................... 14160824

(51) Int. Cl.
| C08F 2/46 | (2006.01) |
| C08F 2/50 | (2006.01) |
| C08G 61/04 | (2006.01) |
| A61K 6/00 | (2006.01) |
| A61K 6/083 | (2006.01) |

(52) U.S. Cl.
CPC ............ *A61K 6/0052* (2013.01); *A61K 6/005* (2013.01); *A61K 6/0008* (2013.01); *A61K 6/0017* (2013.01); *A61K 6/0055* (2013.01); *A61K 6/083* (2013.01); *A61K 6/0835* (2013.01)

(58) Field of Classification Search
CPC .... A61K 6/0052; A61K 6/005; A61K 6/0835; A61K 6/0008; A61K 6/0055; A61K 6/0017; A61K 6/083; C08L 33/06
USPC ............. 522/24, 7, 6, 189, 184, 1, 71; 520/1
See application file for complete search history.

(56) References Cited

U.S. PATENT DOCUMENTS

| 3,991,008 | A | 11/1976 | Temin et al. |
| 4,612,384 | A | 9/1986 | Omura et al. |
| 7,166,651 | B2 | 1/2007 | Qian |
| 7,498,367 | B2 | 3/2009 | Qian |
| 7,541,393 | B2 | 6/2009 | Mitra et al. |
| 7,605,190 | B2 | 10/2009 | Moszner et al. |
| 8,198,343 | B2 | 6/2012 | Liu |
| 8,247,470 | B2 | 8/2012 | Yarimizu et al. |
| 8,829,067 | B2 | 9/2014 | Moszner et al. |
| 2003/0134933 | A1 | 7/2003 | Jin et al. |
| 2007/0040151 | A1* | 2/2007 | Utterodt ............... A61K 6/0017 252/182.13 |
| 2008/0076847 | A1 | 3/2008 | Moszner et al. |
| 2008/0277814 | A1 | 11/2008 | Moszner et al. |
| 2010/0068679 | A1* | 3/2010 | Zappini ................ A61K 6/0044 433/225 |

FOREIGN PATENT DOCUMENTS

WO  WO-2013153166 A1 * 10/2013 ........... A61K 6/0052

OTHER PUBLICATIONS

Rheinberger et al, WO 2013/153166 Machine Translation, Oct. 17, 2013 (Year: 2013).*
International Preliminary Report on Patentability of PCT/EP2015/055858, dated Sep. 20, 2016, 9 pages.

* cited by examiner

*Primary Examiner* — Jessica Whiteley
(74) *Attorney, Agent, or Firm* — Ann M. Knab; Thad McMurray

(57) ABSTRACT

Radically polymerizable dental material which contains as initiator for the radical polymerization a combination of a thiourea derivative and a bisacyldialkylgermanium compound.

17 Claims, No Drawings

PHOTOPOLYMERIZABLE AND DUAL-CURING DENTAL MATERIALS BASED ON THIOUREA DERIVATIVES

CROSS-REFERENCE TO RELATED APPLICATIONS

This application is a National Stage application of International patent application PCT/EP2015/055858 filed on Mar. 19, 2015, which claims priority to European patent application No. 14160824.0 filed on Mar. 20, 2014, the disclosures of which are incorporated herein by reference in their entirety.

The present invention relates to photopolymerizable and dual-curing dental materials, which are suitable in particular for use as dental filling material or fixing cement.

Dental composites usually contain a polymerizable organic matrix and one or more fillers. In most cases, a mixture of monomers, initiator components, stabilizers and pigments is used as polymerizable organic matrix, wherein mixtures of dimethacrylates are often used as monomers. Such materials can be cured by thermal, redox-initiated or light-induced radical polymerization. Acidic monomers are also being used increasingly for the preparation of dental materials. These give the materials self-etching properties and improve their adhesion to the natural tooth substance.

To cure the materials, in the case of indirect filling materials, predominantly thermal initiators, such as e.g. dibenzoyl peroxide (DBPO), or derivatives of barbituric acid, such as e.g. trimethylbarbituric acid, are used. For curing at room temperature, the peroxides are combined with amines such as N,N-dimethyl-sym.-xylidine or N,N-dimethyl-p-toluidine and the barbituric acid derivatives are combined with per-compounds such as e.g. potassium peroxosulphate or per-esters. Both peroxides and barbituric acid derivatives must be stored in the refrigerator due to their limited thermal stability.

α-Diketones such as e.g. camphorquinone (1,7,7-trimethylbicyclo[2.2.1]heptane-2,3-dione) (CQ) and 9,10-phenanthrenequinone have proved worthwhile as photoinitiators for light-curing materials. As a rule, photoinitiators are used together with amines such as 4-(N,N-dimethylamino)benzoic acid ethyl ester as reducing agent. Dual-curing dental materials contain a mixture of a photoinitiator and a redox-initiator system.

The use of amines as initiator component has a series of disadvantages. The oxidation of the amine accelerator can lead to discolorations of the materials. Moreover, amines react easily with acidic substances and are therefore unstable in the presence of acidic monomers.

Redox-initiator systems based on thiourea derivatives exhibit a very good acid-stability.

U.S. Pat. No. 3,991,008 and DE 26 35 595 A1 disclose polymerizable dental filling substances based on methacrylate monomers, which contain as initiator a hydroperoxide oxidizing agent in combination with a substituted thiourea as reducing agent. A preferred oxidizing agent is cumene hydroperoxide, a preferred thiourea derivative is acetylthiourea. The compositions are to be characterized by improved colourfastness and storability and do not need to be stored in a refrigerator. In addition, they are said to have an excellent curing speed.

Self-etching dental materials which contain at least one acidic component in addition to a substituted thiourea and a hydroperoxide are known from EP 1 479 364 A1. The materials are said to have good storage stability and are preferably provided in two-component form, wherein one component contains the substituted thiourea and the second component contains the hydroperoxide. A photoinitiator can be added for the preparation of dual-curing materials.

US 2003/0134933 discloses two-component, self-curing root canal filling materials, which are characterized by a high stability at temperatures of up to 60° C. The materials contain as initiator a hydroperoxide in combination with a thiourea derivative. To accelerate the redox reaction at room temperature, the thiourea-containing component can additionally contain an acidic compound. In order to make it possible to quickly cure the materials in the upper part of the root canal, photoinitiators can be used.

WO 03/057792 A2 describes the use of polymerizable urea and thiourea derivatives as reducing agent in redox-initiator systems. The urea or thiourea compounds in combination with a second reducing agent such as for example ascorbic acid or a non-polymerizable thiourea derivative are said to give a high colour stability as well as good storage stability and curing properties. The reducing agent is combined with an oxidizing agent and optionally with a photoinitiator.

According to EP 1 754 465 A1 it is to be possible to improve the initiator effect of thiourea/hydroperoxide initiator systems by adding catalytic amounts of copper compounds. Copper salts and complexes such as for example copper benzoate, copper di(methacrylate), copper acetylacetonate and copper naphthenate are named as suitable copper compounds.

EP 1 693 046 A1 discloses dental compositions which contain a 2-pyridylthiourea derivative and a hydroperoxide as initiator system. The compositions are to be characterized by a high acid tolerance and be suitable for the preparation of acidic dental primers and adhesives. They can additionally contain customary photoinitiator systems.

WO 2008/134024 A2 proposes the use of cumene hydroperoxide in combination with benzoyl thiourea as initiator system for acidic self-etching dental cements. The effectiveness of this initiator system is not to be impaired by acidic monomers but rather is to be intensified. The compositions can additionally contain a photoinitiator.

EP 2 233 544 A1 discloses two-component, polymerizable dental materials which contain a hydroperoxide and a thiourea derivative as reducing agent and a vanadium compound as accelerator. Moreover, the materials contain a polymer of an α,β-unsaturated mono- or dicarboxylic acid. They are said to have good curability and stability.

Moreover, monomolecular photoinitiators are used, such as for example the commercially available compounds 2,4,6-trimethylbenzoyldiphenylphosphine oxide and bis(2,4,6-trimethylbenzoyl)phenylphosphine oxide. These photoinitiators form radicals in a monomolecular elementary reaction, i.e. by bond cleavage of the photoinitiator.

Latterly, acylgermanes are also being used as photoinitiators for dental materials. EP 1 905 413 A1 discloses acylgermanes which can be activated by visible light in the wavelength range of from 200 to 750 nm. These are characterized by high reactivity and are therefore active even at low concentrations. They are stable in the presence of acidic monomers and, unlike conventional photoinitiators for the visible wavelength range, they do not lead to discolorations of the materials. Acylgermanes can be combined with conventional redox-systems for the preparation of dual-curing materials.

The acylgermane bis(4-methoxybenzoyl)diethylgermanium is already used in commercial products (Ivocerin®—a milestone in composite technology, Ivoclar Vivadent AG, Report 19, 2013).

Cyclic acylgermanium compounds which are suitable as photoinitiators are known from EP 1 905 415 A1.

Acylgermanium compounds which contain several germanium atoms are disclosed in EP 2 103 297 A1.

In spite of the improvements already achieved, there is still a need to further optimize the curing of dental materials.

The object of the invention is to provide dental materials which do not discolour, which have high storage stability at room temperature and are acid-stable and which have improved mechanical properties after curing, i.e. in particular have improved stability in the mouth, abrasion stability and durability. Moreover, materials are to be provided which cure well and allow easy removal of excess material and which have low cytotoxicity.

This object is achieved according to the invention by dental materials which contain a combination of at least one thiourea derivative and at least one bisacyldialkylgermanium compound as initiator for the radical polymerization. Dual-curing dental materials additionally contain a peroxide and preferably a hydroperoxide as additional initiator component.

Thiourea derivatives which are preferred according to the invention are described in U.S. Pat. No. 3,991,008 (column 2, line 35 to column 3, line 14) and in EP 1 754 465 A1 (paragraph [0009]). Particularly preferred thiourea derivatives are methyl, ethyl, allyl, butyl, hexyl, octyl, benzyl, 1,1,3-trimethyl, 1,1-diallyl, 1,3-diallyl, 1-(2-pyridyl)-2-thiourea, acetyl, propanoyl, butanoyl, pentanoyl, hexanoyl, heptanoyl, octanoyl, nonanoyl, decanoyl and benzoyl thiourea, wherein acetyl and hexanoyl thiourea are quite particularly preferred.

Preferred bisacyldialkylgermanium compounds are described in EP 1 905 413 A1, EP 1 905 415 A1 and EP 2 103 297 A1, wherein bisacylgermanes according to Formula (II) of EP 1 905 413 A1 are particularly preferred. Quite particularly preferred bisacyldialkylgermanium compounds are bisbenzoyldiethylgermanium, bisbenzoyldimethylgermanium, bisbenzoyldibutylgermanium, bis(4-methoxybenzoyl)dimethylgermanium and bis(4-methoxybenzoyl)diethylgermanium, wherein bis(4-methoxybenzoyl)diethylgermanium is most preferred.

Preferred hydroperoxides are 1,1,3,3-tetramethylbutyl hydroperoxide, t-butylhydroperoxide, cumene hydroperoxide, pinane hydroperoxide, p-menthane hydroperoxide, diisopropylbenzene hydroperoxide and t-amyl hydroperoxide, wherein cumene hydroperoxide is particularly preferred.

It was surprisingly found that the curing of dental materials could be improved using a mixture of a bisacyldialkylgermanium compound as photoinitiator and a thiourea derivative. The materials according to the invention are characterized in particular by a high degree of curing, high surface hardness and abrasion stability, good material stability in the presence of saliva and durability.

Photopolymerizable dental materials are preferably present as one-component systems, i.e. in the form of a mixture which contains all the constituents of the dental material. They contain exclusively a photoinitiator as initiator and can be cured by irradiation with light.

In addition to the photoinitiator, dual-curing dental materials additionally contain a peroxide, preferably a hydroperoxide as oxidizing agent. Dual-curing materials are preferably present in the form of two separate components, as otherwise a premature curing would take place, wherein the first component contains the (hydro)peroxide and the second component contains the thiourea derivative. The thiourea derivative serves as reducing agent (accelerator). The components are correspondingly also called catalyst paste and accelerator paste.

The curing of the dual-curing materials can be activated by mixing the catalyst and accelerator pastes. The composition is adjusted such that it still remains processable for a few minutes after the pastes are mixed (so-called processing time), but cures rapidly after the processing. The processing and curing times can be adjusted primarily through the type and concentration of (hydro)peroxide, thiourea derivative and optionally by the addition of further components such as a transition metal redox catalyst and inhibitor.

As a rule, a polymerization activated by redox-initiator systems proceeds more slowly than a photopolymerization. Correspondingly, excesses can be removed easily in the case of dual-curing materials, by the radiation-activated photopolymerization is only carried out after excesses have been removed.

The dental materials according to the invention contain a radically polymerizable matrix. As polymerizable matrix, radically polymerizable monomers or mixtures of radically polymerizable monomers are preferred, in particular one or more (meth)acrylates, particularly preferably a mixture of mono- and polyfunctional methacrylates, quite particularly preferably of mono- and difunctional methacrylates. By monofunctional (meth)acrylates are meant compounds with one, by polyfunctional (meth)acrylates compounds with two or more, preferably 2 to 4, radically polymerizable groups.

Preferred mono- or polyfunctional methacrylates are methyl, ethyl, 2-hydroxyethyl, butyl, benzyl, tetrahydrofurfuryl or isobornyl (meth)acrylate, p-cumylphenoxyethylene glycol methacrylate (CMP-1E), bisphenol A dimethacrylate, bis-GMA (an addition product of methacrylic acid and bisphenol A diglycidyl ether), ethoxylated or propoxylated bisphenol A dimethacrylate, such as e.g. the bisphenol A dimethacrylate SR-348c with 3 ethoxy groups or 2,2-bis[4-(2-methacryloxypropoxy)phenyl]propane, UDMA (an addition product of 2-hydroxyethyl methacrylate (HEMA) and 2,2,4-trimethylhexamethylene diisocyanate), TMX-UDMA (an addition product of a mixture of HEMA and hydroxypropyl methacrylate (HPMA) with $\alpha,\alpha,\alpha',\alpha'$-tetramethyl-m-xylylene diisocyanate (TMXDI), di-, tri- or tetraethylene glycol dimethacrylate, trimethylolpropane trimethacrylate, pentaerythritol tetramethacrylate, as well as glycerol di- and trimethacrylate, 1,4-butanediol dimethacrylate, 1,10-decanediol dimethacrylate ($D_3MA$) or 1,12-dodecanediol dimethacrylate. Particularly suitable are mixtures of CMP-1E, UDMA, and TMX-UDMA as well as glycerol di- or glycerol trimethacrylate and/or $D_3MA$.

According to the invention, a monomer mixture is preferably used which contains at least one low-volatile monomethacrylate, at least one highly viscous poly-, preferably difunctional methacrylate and at least one low-viscosity poly-, preferably difunctional methacrylate.

According to the invention by low-volatile monomers are meant compounds with a boiling point >150° C. at normal pressure. The boiling point can e.g. be determined using a distillation apparatus. By highly viscous monomers are meant substances with a viscosity ≥5 Pa·s, preferably from 5 to 10,000 Pa·s and particularly preferably from 5 to 2,000 Pa·s and by low-viscosity monomers are meant substances with a viscosity ≤300 mPa·s, preferably from 1 to 300 mPa·s and particularly preferably from 30 to 300 mPa·s, wherein the viscosity is determined using a capillary viscometer (low viscosity) or rotating viscometer (high viscosity) at a temperature of 25° C.

Particularly preferred highly viscous dimethacrylates are TMX-UDMA (an addition product of HEMA and hydroxypropyl methacrylate (HPMA) with α,α,α',α'-tetramethyl-m-xylylene diisocyanate (TMXDI)) and 1,6-bis-[2-methacryloyloxyethoxycarbonylamino]-2,4,4-trimethylhexane (UDMA). Preferred low-viscosity dimethacrylates which are used as diluting monomers are bismethacryloyloxymethyltricyclo[5.2.1.]decane (TCDMA), glycerol dimethacrylate (GDMA) and in particular decanediol-1,10-dimethacrylate ($D_3MA$). A particularly preferred low-volatile monomethacrylate is p-cumylphenoxyethylene glycol methacrylate (CMP-1E).

According to an embodiment the dental materials according to the invention contain, in addition to the above-named monomers, one or more acid-group-containing radically polymerizable monomers (adhesive monomers). These give the materials self-adhesive and/or self-etching properties.

Preferred acid-group-containing monomers are polymerizable carboxylic acids, phosphonic acids, phosphoric acid esters and sulphonic acids.

Preferred carboxylic acids are maleic acid, acrylic acid, methacrylic acid, 2-(hydroxymethyl)acrylic acid, 4-(meth)acryloyloxyethyl trimellitic acid, 10-methacryloyloxydecylmalonic acid, N-(2-hydroxy-3-methacryloyloxypropyl)-N-phenylglycine and 4-vinylbenzoic acid.

Preferred phosphonic acid monomers are vinylphosphonic acid, 4-vinylphenylphosphonic acid, 4-vinylbenzylphosphonic acid, 2-methacryloyloxyethylphosphonic acid, 2-methacrylamidoethylphosphonic acid, 4-methacrylamido-4-methylpentylphosphonic acid, 2-[4-(dihydroxyphosphoryl)-2-oxa-butyl]-acrylic acid or 2-[4-(dihydroxyphosphoryl)-2-oxa-butyl]-acrylic acid ethyl and -2,4,6-trimethylphenyl ester.

Preferred acidic polymerizable phosphoric acid esters are 2-methacryloyloxypropyl mono- or dihydrogen phosphate, 2-methacryloyloxyethyl mono- or dihydrogen phosphate, 2-methacryloyloxyethylphenyl hydrogen phosphate, dipentaerythritolpentamethacryloyloxyphosphate, 10-methacryloyloxydecyl dihydrogen phosphate, phosphoric acid mono-(1-acryloyl-piperidine-4-yl)-ester, 6-(methacrylamido)hexyl dihydrogen phosphate and 1,3-bis-(N-acryloyl-N-propyl-amino)-propan-2-yl dihydrogen phosphate.

Preferred polymerizable sulphonic acids are vinyl sulphonic acid, 4-vinylphenyl sulphonic acid or 3-(methacrylamido)propyl sulphonic acid.

Particularly preferred adhesive monomers are 4-(meth)acryloyloxyethyl trimellitic acid, 2-[4-(dihydroxyphosphoryl)-2-oxa-butyl]-acrylic acid ethyl or -2,4,6-trimethylphenyl ester and 10-methacryloyloxydecyl dihydrogen phosphate.

Furthermore, the dental materials according to the invention preferably also contain organic or particularly preferably inorganic particulate fillers. Fillers based on oxides are preferred, such as $SiO_2$, $ZrO_2$ and $TiO_2$ or mixed oxides of $SiO_2$, $ZrO_2$, ZnO and/or $TiO_2$, nanoparticulate or microfine fillers such as pyrogenic silicic acid or precipitated silicic acid (weight-average particle size of 10-1,000 nm) as well as mini fillers, such as quartz, glass ceramic or X-ray opaque glass powder from e.g. barium or strontium aluminium silicate glasses (weight-average particle size of 0.2-10 μm). Further fillers are X-ray opaque fillers, such as ytterbium trifluoride or nanoparticulate tantalum(V) oxide or barium sulphate or mixed oxides of $SiO_2$ with ytterbium(III) oxide or tantalum(V) oxide (weight-average particle size of 10-1,000 nm).

To improve the bond between the filler particles and the crosslinked polymerization matrix, $SiO_2$-based fillers can be surface-modified with methacrylate-functionalized silanes, such as e.g. 3-methacryloyloxypropyltrimethoxysilane. For the surface-modification of non-silicate fillers, e.g. of $ZrO_2$ or $TiO_2$, functionalized acidic phosphates, such as e.g. 10-methacryloyloxy dihydrogen phosphate can also be used.

Dental materials containing filler are particularly suitable as dental filling composites and cements. Materials which only contain fillers with a maximum particle size of less than 600 nm are particularly preferred. These are particularly suitable as dental cements.

Optionally, the compositions used according to the invention can contain further additives, above all stabilizers, such as e.g. polymerization stabilizers, dyes, microbiocidal active ingredients, fluoride-ion-releasing additives, optical brighteners, fluorescent agents, plasticizers, transition metal redox catalysts and/or UV absorbers.

Compounds of transition metals which have at least two stable valency stages are particularly suitable as transition metal redox catalysts. They are, above all, compounds of the elements copper, iron, vanadium, nickel or cobalt, wherein copper compounds are particularly preferred, and these metals are preferably used as highly organosoluble compounds, such as e.g. acetylacetonate, naphthenate or 2-ethylhexanoate. These catalysts accelerate the redox reaction of oxidizing and reducing agents and thus the formation of radicals, i.e. e.g. the redox reaction of hydroperoxide and thiourea derivative.

Dental materials which additionally comprise such a transition metal catalyst are preferred according to the present invention. These redox catalysts are preferably used in an amount of 10 to 100 ppm, particularly preferably 20 to 80 ppm and most preferably 30 to 80 ppm, based on the total weight of the dental material.

According to the invention, those dental materials which have the following composition are preferred:

(a) 2.0 to 20 wt.-%, particularly preferably 5 to 15 wt.-% of one or more monomethacrylates,
(b) 5.0 to 60 wt.-%, particularly preferably 10 to 40 wt.-% of one or more dimethacrylates,
(c) 0 to 15 wt.-%, particularly preferably 0 to 10 wt.-% of one or more acid-group-containing adhesive monomers,
(d) 20 to 90 wt.-%, particularly preferably 40 to 80 wt.-% filler(s),
(e) 0.01 to 4.0 wt.-%, particularly preferably 0.1 to 2.0 wt.-% thiourea derivative(s),
(f) 0 to 3.0 wt.-%, particularly preferably 0.1 to 2.0 wt.-% hydroperoxide(s),
(g) 0.001 to 1.0 wt.-%, particularly preferably 0.005 to 0.5 wt.-% bisacyldialkylgermanium compound(s),
(h) 0.1 to 5.0 wt.-%, particularly preferably 0.1 to 2.0 wt.-% additive(s).

Dental materials are particularly preferred which have the following composition:

(a) 2.0 to 20 wt.-%, particularly preferably 5 to 15 wt.-% of one or more low-volatile monomethacrylates;
(b1) 5.0 to 25 wt.-%, particularly preferably 5 to 15 wt.-% of one or more highly viscous dimethacrylates,
(b2) 5 to 30 wt.-%, particularly preferably 10 to 20 wt.-% of one or more low-viscosity dimethacrylates,
(c) 0 to 15 wt.-%, particularly preferably 0 to 10 wt.-% of one or more acid-group-containing adhesive monomers,
(d) 20 to 90 wt.-%, particularly preferably 40 to 80 wt.-% filler(s),
(e) 0.01 to 4.0 wt.-%, particularly preferably 0.1 to 2.0 wt.-% thiourea derivative(s),
(f) 0 to 3.0 wt.-%, particularly preferably 0.1 to 2.0 wt.-% hydroperoxide(s), (g) 0.001 to 1.0 wt.-%, particularly preferably 0.005 to 0.5 wt.-% bisacyldialkylgermanium compound(s), (h) 0.1 to 5.0 wt.-%, particularly preferably 0.1 to 2.0 wt.-% additive(s).

As explained above, the dental materials preferably comprise 10 to 100 ppm, particularly preferably 20 to 80 ppm and most preferably 30 to 80 ppm of a transition metal catalyst. These ranges apply to the preferred compositions as well as to the particularly preferred compositions.

Dual-curing materials contain 0.1 to 3.0 wt.-%, particularly preferably 0.1 to 2.0 wt.-% peroxide(s), preferably hydroperoxide(s). The dental materials according to the invention can be provided in a one- or two-component form. Dual-curing materials preferably have two components, i.e. they contain two separate components which are mixed with one another before being used. The composition of the components is chosen such that, after mixing, materials with the total composition defined above are obtained.

Those dental materials which consist of the named substances are quite particularly preferred. Furthermore preferred are those materials in which the individual substances in each case are selected from the above-named preferred and particularly preferred substances. Materials are particularly preferred which do not contain any amines such as e.g. amine accelerators. Likewise, materials are preferred which do not contain any TEGDMA and preferably also do not contain any bis-GMA.

The dental materials according to the invention are particularly suitable as dental cements, filling composites and veneering materials, and as materials for preparing inlays, onlays, crowns and bridges. The materials preferably only contain fillers with a maximum particle size of <600 nm. They permit the preparation of dental materials with low surface roughness and high gloss as well as excellent abrasion stability.

The dental materials are suitable primarily for intraoral use by the dentist to restore damaged teeth (clinical materials). However, they can also be used extraorally, for example in the preparation or repair of dental restorations (technical materials).

The invention is explained in more detail below by means of examples.

EXAMPLES

Examples 1-8

Light-Curing Composites Based on an Initiator Composition According to the Invention Corresponding to Table 1 set out below, composites were prepared (all values given in mass-%) based on 44.5% of a silanized $SiO_2$ mixed oxide with a content of 30% $ZrO_2$), 20% ytterbium fluoride and 35.5% of a methacrylate mixture (20% CMP-1E, 20% GDMA, 20% TMX-UDMA, 25% UDMA and 14.5% $D_3MA$ as well as 0.5% BHT as stabilizer). The components detailed in Table 1 were contained as initiator system. The composites were prepared using a kneader (Linden). To measure the Vickers hardness, metal moulds (h=2 mm, Ø=10 mm) were filled with composite and covered with a PET film. The polymerization was carried out by irradiation from above with a polymerization lamp (LED Bluephase; Ivoclar Vivadent AG; 10 s at 650 mW/cm²).

After preparation, the test pieces were stored in a drying oven at 37° C. for 24 h and then the illuminated upper side of the test pieces was ground flat first with a 2500, then with a 4000 abrasive paper and finally polished with polishing paste. The Vickers hardness was measured on the polymerized upper side with a universal hardness tester (model ZHU0.2; Zwick/Röll). 3 individual measurements were carried out on each test piece. The resulting average values are given in Table 1.

The results demonstrate that composites which contain a thiourea derivative in addition to a Ge photoinitiator (Ivocerin®) have a significantly increased Vickers hardness compared with composites which contain amine accelerator (EMBO or DABA). This means high abrasion stability and makes it possible to prepare dental restorations with high surface smoothness, high gloss and improved stability in the mouth.

TABLE 1

Initiator content in the monomer of the composites and Vickers hardness

| Ex. | Ivocerin ®[1] [wt.-%] | ATU[2]/Cu[3] [wt.-%] | Amine [wt.-%] | Vickers hardness (MPa) |
|---|---|---|---|---|
| 1*) | 0.035 | 0 | 0 | 92.64 ± 4.3 |
| 2 | 0.035 | 1.50/65 | 0 | 129.1 ± 7.7 |
| 3*) | 0.050 | 0 | 0 | 206.2 ± 9.7 |
| 4 | 0.050 | 1.50/65 | 0 | 242.8 ± 10.1 |
| 4a*) | 0 | 1.50/65 | 0 | does not polymerize |
| 4b*) | 0 | 1.50/0 | 0 | does not polymerize |
| 5*) | 0.035 | 0 | 0.5/EMBO[4] | 94.0 ± 2.1 |
| 5a*) | 0.035 | 0 | 1.5/EMBO[4] | 98 ± 11.5 |
| 6*) | 0.035 | 0 | 0.5/DABA[5] | 100.0 ± 5.8 |
| 6a*) | 0.035 | 0 | 1.5/DABA[5] | 95 ± 0.5 |
| 7*) | 0.050 | 0 | 0.5/EMBO[4] | 210.3 ± 15.5 |
| 8*) | 0.050 | 0 | 0.5/DABA[5] | 196.4 ± 8.4 |

*)Comparison example
[1] Bis-(4-methoxybenzoyl)diethylgermanium (Ivoclar Vivadent AG)
[2] 1-Acetylthiourea
[3] Cu-acetylacetonate (Cu content in ppm)
[4] (4-Dimethylamino)benzoic acid ethyl ester
[5] N,N-diethyl-3,5-di-tert-butylaniline

The invention claimed is:

1. A radically polymerizable dental material which comprises an initiator for the radical polymerization, wherein the initiator comprises a combination of a thiourea derivative and a bisacyldialkylgermanium compound,
   wherein the thiourea derivative is selected from methyl, ethyl, allyl, butyl, hexyl, octyl, benzyl, 1,1,3-trimethyl, 1,1-diallyl, 1,3-diallyl, 1-(2-pyridyl)-2-thiourea, acetyl, propanoyl, butanoyl, pentanoyl, hexanoyl, heptanoyl, octanoyl, nonanoyl, decanoyl, benzoyl thiourea or a mixture thereof; and
   wherein said radically polymerizable dental material comprises as a polymerizable matrix a mixture of radically polymerizable monomers which comprises at least one highly viscous difunctional methacrylate which is selected from TMX-UDMA (an addition product of HEMA and hydroxypropyl methacrylate (HPMA) with α,α,α',α'-tetramethyl-m-xylene diisocyanate (TMXDI)) and 1,6-bis-[2-methacryloyloxyethoxycarbonylamino]-2,4,4-tri¬methylhexane (UDMA); at least one low-viscosity difunctional methacrylate which is selected from bismethacryloyloxymethyltricyclo[5.2.1]decane (TCDMA), glycerol dimethacrylate (GDMA) and/or decanediol-1,10-dimethacrylate (D3MA); and p-cumylphenoxyethylene glycol methacrylate (CMP-1E) as a low-volatile monomethacrylate.

2. The dental material according to claim 1, which comprises as the bisacyldialkylgermanium compound, bisbenzoyldiethylgermanium, bisbenzoyldimethylgermanium, bisbenzoyldibutylgermanium, bis(4-methoxybenzoyl)

dimethylgermanium, bis(4-methoxybenzoyl)diethylgermanium or a mixture thereof.

3. The dental material according to claim 1, which additionally comprises a hydroperoxide.

4. The dental material according to claim 3, which comprises as the hydroperoxide, 1,1,3,3-tetramethylbutyl hydroperoxide, t-butyl hydroperoxide, cumene hydroperoxide, pinane hydroperoxide, p-menthane hydroperoxide, diisopropylbenzene hydroperoxide, t-amyl hydroperoxide or a mixture thereof.

5. The dental material according to claim 1, which additionally comprises organic or inorganic particulate filler.

6. The dental material according to claim 5, which comprises filler with a maximum particle size of less than 600 nm.

7. The dental material according to claim 1, which comprises
(a) 2.0-20 wt.-% of said low-volatile monomethacrylate,
(b1) 5.0-25 wt.-% of said highly viscous dimethacrylates,
(b2) 5-30 wt.-% of said low-viscosity dimethacrylates,
(e) 0.01-4.0 wt.-% of said thiourea derivative,
(g) 0.001-1.0 wt.-% of said bisacyldialkylgermanium compound,
said composition further comprising
(c) 0-15 wt.-% of one or more acid-group-containing adhesive monomers,
(d) 20-90 wt.-% filler(s),
(f) 0-3.0 wt.-% hydroperoxide(s),
(h) 0.1-5.0 wt.-% additive(s).

8. The dental material according to claim 1, which further comprises 10 to 100 ppm of a redox catalyst.

9. The dental material according to claim 1, which is free from TEGDMA and bis-GMA.

10. The dental material according to claim 1, which is free from amines.

11. A method of using of a dental material according to claim 1 as dental cement, filling composite, veneering material, as materials for preparing inlays, onlays, crowns or bridges comprising preparing the ingredients according to claim 7 and applying the ingredients as a dental cement, filling composite, veneering material.

12. The dental material according to claim 1, which comprises
(a) 5-15 wt.-% of said low-volatile monomethacrylate,
(b1) 5-15 wt.-% of said highly viscous dimethacrylates,
(b2) 10-20 wt.-% of said low-viscosity dimethacrylates,
(e) 0.1-2.0 wt.-% of said thiourea derivative,
(g) 0.005-0.5 wt.-% of said bisacyldialkylgermanium compound,
said composition further comprising
(c) 0-10 wt.-% of one or more acid-group-containing adhesive monomers,
(d) 40-80 wt.-% filler(s),
(f) 0.1-2.0 wt.-% hydroperoxide(s),
(h) 0.1-2.0 wt.-% additive(s).

13. The dental material according to claim 1, which further comprises 20 to 80 ppm of a redox catalyst.

14. The dental material according to claim 1, which comprises 30 to 80 ppm of a redox catalyst.

15. The dental material according to claim 1, which comprises TMX-UDMA.

16. The dental material according to claim 1, which comprises CMP-1E.

17. The dental material according to claim 1, which comprises TMX-UDMA and CMP-1E.

* * * * *